United States Patent [19]
Carlsson

[11] Patent Number: 6,093,870
[45] Date of Patent: Jul. 25, 2000

[54] ABSORBENT ARTICLE, SUCH AS A DIAPER, AN INCONTINENCE GUARD, A SANITARY NAPKIN OR LIKE ARTICLE

[75] Inventor: Anders Carlsson, Mölnlycke, Sweden

[73] Assignee: SCA Molnlycke AB, Goteborg, Switzerland

[21] Appl. No.: 08/945,019

[22] PCT Filed: Jun. 14, 1996

[86] PCT No.: PCT/SE96/00778

§ 371 Date: Dec. 10, 1997

§ 102(e) Date: Dec. 10, 1997

[87] PCT Pub. No.: WO97/01995

PCT Pub. Date: Jan. 23, 1997

[30] Foreign Application Priority Data

Jun. 30, 1995 [SE] Sweden .................................. 9502390

[51] Int. Cl.[7] ...................................... A61F 13/15

[52] U.S. Cl. ............................ 604/368; 604/358; 604/378
[58] Field of Search ..................................... 604/368, 378, 604/385.1, 358

[56] References Cited

U.S. PATENT DOCUMENTS

| | | |
|---|---|---|
| 4,560,372 | 12/1985 | Pieniak . |
| 4,676,784 | 6/1987 | Erdman et al. . |
| 5,713,881 | 2/1998 | Rezai et al. ............................. 604/368 |
| 5,868,724 | 2/1999 | Dierckes, Jr. et al. ................. 604/368 |

*Primary Examiner*—John G. Weiss
*Assistant Examiner*—Dennis Ruhl
*Attorney, Agent, or Firm*—Young & Thompson

[57] ABSTRACT

An absorbent article, such as a diaper, an incontinence guard or a sanitary napkin, which includes a superabsorbent material in film or band form which has slots disposed therein. The film or band is stretched transversely to the longitudinal direction of the slots, such as to form openings.

10 Claims, 1 Drawing Sheet

ABSORBENT ARTICLE, SUCH AS A DIAPER, AN INCONTINENCE GUARD, A SANITARY NAPKIN OR LIKE ARTICLE

BACKGROUND OF THE INVENTION

An absorbent article such as a diaper, a sanitary napkin or an incontinence guard will normally include a liquid-permeable outer sheet, a liquid-impervious barrier sheet and an absorbent body located therebetween. An absorbent article of one of the aforesaid kinds has a generally rectangular shape, including two long sides and two short sides.

The outer sheet is that part of the absorbent body which lies proximal to the wearer's body in use, while the barrier layer is that part of the absorbent article which lies distal from the wearer's body. The outer sheet is normally comprised of perforated plastic film, nonwoven or a plastic and nonwoven laminate. The plastic may be a thermoplastic material, such as polyethylene. The nonwoven material may be comprised of natural fibres, such as cellulose or cotton fibres, or synthetic fibres, such as polyethylene, polypropylene, polyurethane, nylon or regenerated cellulose fibres.

The purpose of the outer sheet of an absorbent article of the aforesaid kind is to conduct fluid into the article, and to prevent rewetting of the wearer's skin and therewith create a dry surface in contact with the skin. A dry surface on that part of the article which lies against the wearer's skin in use is important to the comfort of the wearer and also in avoiding skin irritation.

The barrier layer is produced in a liquid-impermeable material and functions to prevent liquid leaking from the underside of the absorbent article. The barrier layer may be comprised of any type of material that will fulfil the criterion of liquid impermeability and which is sufficiently flexible for the purpose intended. Examples of suitable barrier layer materials are plastic films, nonwoven and laminates thereof. The plastic film may be comprised, for instance, of polyethylene, polypropylene or polyester.

The absorbent body is normally produced from cellulose pulp. The pulp may exist in rolls, bales or sheets that have been dry-defibrated and transformed in a fluffed state to a pulp mat. As before mentioned, the absorbent body may be comprised of cellulose fibres. Examples of other fibres conceivable in this regard are cotton fibres and synthetic fibres. It is also known to use in the absorbent body a foamed material.

So-called superabsorbents are sometimes used with the intention of enhancing the liquid-retaining capacity of the absorbent body, superabsorbents being polymers that are capable of absorbing several times their own weight of water or body fluid. Examples of such superabsorbents are polyacrylates, starch or modified cellulose, such as carboxymethyl cellulose.

The superabsorbent is normally added to the absorbent material in powder form, and is either admixed uniformly or is concentrated to certain parts of the absorbent body. The superabsorbent can also be supplied to the absorbent body in the form of a band or a film. The advantage with this method of administration is that the superabsorbent can be easily applied in the intended manner and in the correct amount. Application of the superabsorbent in the form of a film or band also avoids the potentially harmful dust that is generated when handling all types of powder material.

The drawback with superabsorbent in film or band form, is that this method of administration can easily result in so-called gel-blocking. Gel-blocking occurs because of the rapid swelling of the superabsorbent when liquid is applied, therewith preventing further spreading of liquid down through the absorbent body. Naturally, this can also occur when the superabsorbent is applied in powder form, although the risk of gel-blocking is naturally greater when the superabsorbent has been concentrated to a smaller area of the absorbent body, as is the case when applying superabsorbent in a film or band form.

OBJECT OF THE INVENTION

The object of the present invention is to alleviate the aforesaid problems associated with application, dust generation and gel-blocking in conjunction with the use of superabsorbents in absorbent articles.

SUMMARY OF THE INVENTION

The aforesaid problems associated with superabsorbent administration are solved by means of the present invention by applying the superabsorbent in the form of a film or a band that has been provided with slots and stretched transversely to the direction of the slots. This results in a superabsorbent band or film having a three-dimensional structure and including holes.

It is known to produce superabsorbent material in a film form for use in absorbent articles, such as incontinence guards. U.S. Pat. No. 4,643,726 describes an insert for use as an incontinence guard, which is intended to be worn in conventional under-clothes. The insert includes an inner liquid-permeable nonwoven sheet, an outer sheet of liquid-impermeable polyethylene film, a single absorbent layer of fluffed cellulose placed therebetween, and a layer of superabsorbent polymer located between the inner sheet and the absorbent layer. The layer of superabsorbent polymer is perforated, to facilitate passage of liquid down through the layer.

U.S. Pat. No. 4,560,372 discloses a disposable absorbent product such as a diaper, sanitary napkin or wound dressing. This product includes an absorbent body and a superabsorbent material in band or film form applied in said body or in close proximity thereof; which band or film is slotted and stretched transversely to the longitudinal direction of the slots so that these form wider openings with parts of band material located between the openings. Although these slot openings, or the perforations describe in U.S. Pat. No. 4,643,726, prevent gel-blocking to some extent, at least on the first wetting occasion, the openings will gradually decrease in size as the layer is wetted, due to swelling of the superabsorbent material. The liquid influx time will therefore decrease markedly with repeated wetting of the layer.

According to the present invention, the slotted superabsorbent band or film may include a large number of through-penetrating slots or slits. As the band or the film is stretched transversely to the longitudinal direction of the slots, the slots will open by virtue of the material on opposite sides of respective slots being twisted out of the plane of the film or band to form surfaces which are raised or sunken respectively from the plane of the layer. The slots are preferably straight, although they may also have some other suitable form which will allow the layer parts adjacent the slots to be twisted out of the plane of the layer and therewith form upraised edges when the film or the band is stretched. When the slots are mutually displaced in the aforedescribed manner, the edges of the slots will be lifted as the band or the film is stretched transversely to the longitudinal direction of the slots, such that the material will transform from a two-dimensional structure to a three-dimensional network structure in which the widened slots form rhomboidal openings.

Because the edges of the openings will be located in different planes, a large open area is obtained, and the openings will not swell together as the surface is wetted to the same extent as if the edges of the openings were located in one and the same plane. The openings thus maintain a wide open area even after wetting the layer, thereby preventing gel-blocking and achieving a high liquid influx rate, even after repeated wetting of the layer.

In one conceivable method of producing an absorbent article that includes an absorbent body made of fluff pulp in accordance with the present invention, there is first formed a pulp mat core. The slotted and stretched superabsorbent film is then placed on the pulp core and a second mat core is formed on top of and through the superabsorbent film. There is obtained in this way a product which is permeable to extremes beyond the superabsorbent film or band. Thus, when forming the mats, the pulp fibres will place themselves in the openings formed in the slotted and stretched superabsorbent film. This assists the transportation of liquid beyond the superabsorbent film and also in spreading of liquid to different parts thereof.

In another conceivable method of manufacturing an absorbent article in accordance with the invention, the band or film of superabsorbent material is placed directly adjacent the absorbent body on that side thereof which is intended to lie against the wearer in use. An outer sheet is then placed on top of the superabsorbent film.

In another conceivable method of manufacturing an absorbent article in accordance with the present invention, the band or the film of superabsorbent material is placed directly adjacent the absorbent body on that side thereof which is intended to face towards the barrier layer.

The invention is not limited to absorbent articles which include an absorbent body comprised of mat-formed cellulose, but can also be applied with other types of absorbent bodies, such as absorbent bodies made from foamed material or cellulose material from pre-formed webs.

BRIEF DESCRIPTION OF THE DRAWINGS

The invention will now be described in more detail with reference to exemplifying embodiments thereof and also with reference to the accompanying drawings. The invention is not limited to the described and illustrated exemplifying embodiments nor to the drawings themselves, which are merely intended to explain and illustrate the invention.

DETAILED DESCRIPTION OF THE INVENTION

Figure 1:
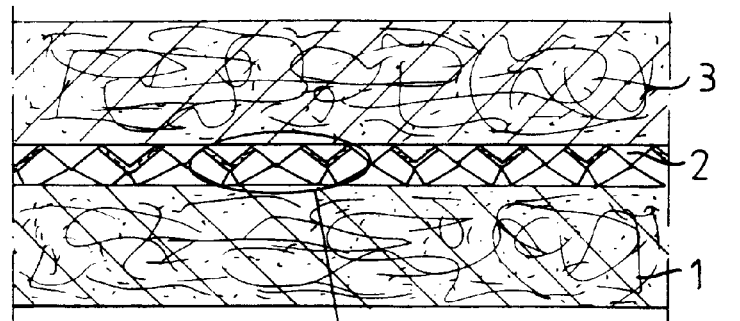
FIG. 1 is a cross-sectional view of a band of superabsorbent material which includes slots.

FIG. 1 illustrates an absorbent body constructed in accordance with the invention. The body may be produced by mat-forming a first pulp core 1 or pulp layer. The previously slotted and extended superabsorbent band 2 is placed on top of the first pulp core 1, whereafter a second pulp core 3 or pulp layer is formed on top of the band 2. When using a superabsorbent band constructed in accordance with the invention, there is obtained when mat-forming the second pulp core an absorbent body whose pulp fibres will extend through the holes formed in the superabsorbent band 2 as the band is stretched and the slots consequently opened. This results in a product which is highly permeable to liquid through the superabsorbent band 2.

The slotted band or film 2 of superabsorbent material is applied in the absorbent product in a stretched state, more specifically while stretched in a direction transversely to the longitudinal direction of the slots. The material 4 located on both sides of each slot is therewith twisted or rotated out of the plane of the film or band to form edges 5 which project upwardly and downwardly from said plane. The thus widened slots form rhomboidal openings 6 whose size will depend on the extent to which the band or film is stretched. Preferably, the openings 6 will lie in a row opposite the spaces between the openings in adjacent rows.

The distance between the slots in the longitudinal direction will preferably be smaller than 1.5 times the length of a slot, suitably less than or equal to the slot length, preferably smaller than the slot length.

The distance between mutually adjacent rows of slots will preferably be smaller than 1.5 times the slot length, suitably smaller than or equal to the slot length, preferably smaller than the slot length.

The slot film or band 2 may either be applied so as to cover the whole of the absorbent core, or so as to cover only parts thereof. For instance, the film or band 2 may be applied so as to cover only the anticipated wetting region of the absorbent article and regions that border on said wetting region. It is also conceivable to provide the film or the band with one or more larger openings in the vicinity of the anticipated wetting region, so as to thereby enhance the liquid-permeability of this region of the article. It is also conceivable to vary the lengths of the slots in different regions, such that the slots will have a greater length, therewith providing larger openings, for instance in those regions where the heaviest influx of liquid can be expected to occur.

Figure 2:
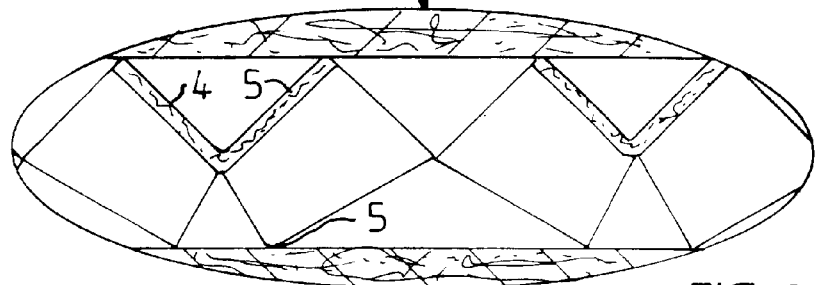
FIG. 2 is a sectional view in larger scale of the extended or stretched slotted material.
Figure 3:
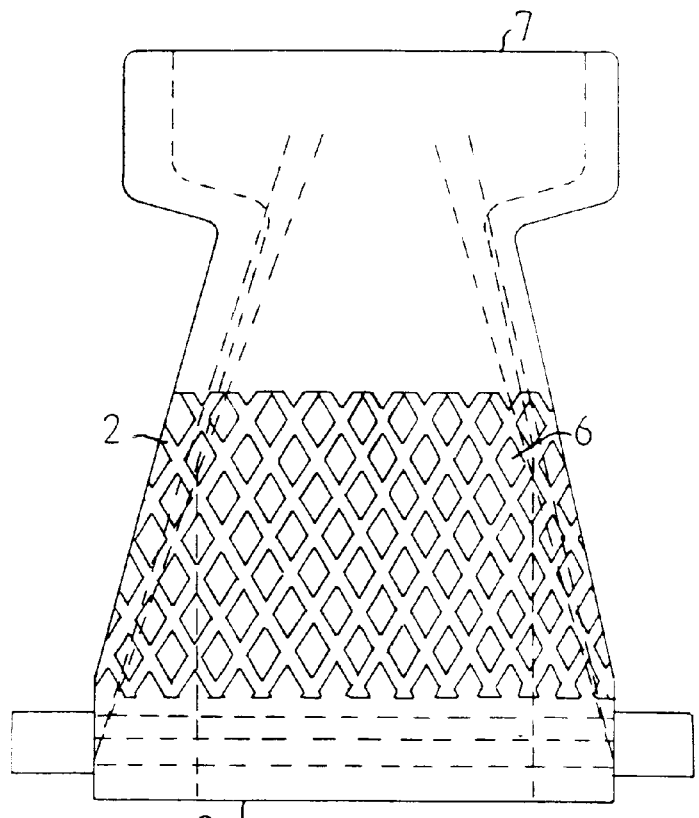
FIG. 3 is a view of the extended or stretched slotted material from above.

FIG. 3 shows a diaper which includes a slotted film of superabsorbent material. The diaper is seen from that side which is intended to face towards the wearer in use, having a part 7 which is intended to lie against the wearer's stomach and a part 8 which is intended to lie against the wearer's back. The slotted film 2 would not normally be visible, although FIG. 2 shows a section of the diaper in which the outer sheet and possible overlying absorbent body have been lifted away to enable the slotted film 2 to be seen from above.

I claim:

1. An absorbent article selected from the group consisting of a diaper, an incontinence guard and a sanitary napkin, the absorbent article comprising: an absorbent body, and a superabsorbent material applied in said body or in close proximity thereof, said superabsorbent material including a plurality of slots extending in a longitudinal direction, said superabsorbent material being stretched transversely to the longitudinal direction of the slots so that said slots form openings with parts of the superabsorbent material located between the openings, said slots of superabsorbent material extending in a plane in a non-stretched state, and said parts of superabsorbent material located between the openings being twisted or rotated to form respectively upwardly and downwardly projecting edges with respect to said plane.

2. The absorbent article according to claim 1, wherein the slots are disposed in longitudinally extending rows which are generally parallel to the longitudinal direction.

3. The absorbent article according to claim 1, wherein the slots are disposed in rows which are generally transversal to the longitudinal direction.

4. The absorbent article according to claim 1, wherein the openings of a first row lie opposite spaces between the openings of adjacent rows.

5. The absorbent article according to claim 1, wherein the distance between ends of two mutually sequential slots is smaller than 1.5 times the length of a slot.

6. The absorbent article according to claim 2, wherein the distance between the rows is smaller than 1.5 times the length of the slot.

7. The absorbent article according to claim 1, wherein the superabsorbent material is in the form of a band or film, and is disposed in only a part of at least one of the length and the width of the absorbent body.

8. The absorbent article according to claim 1, wherein the superabsorbent material includes at least one open area of greater dimension than each of the openings.

9. The absorbent article according to claim 1, wherein the length of the slots and therewith the size of the openings, vary in different regions of the superabsorbent material.

10. A method of manufacturing an absorbent structure for use in an absorbent article selected from the group consisting of a diaper, an incontinence guard and a sanitary napkin, which comprises:

providing a plurality of through slits in a superabsorbent material, which in a non-stretched state of the superabsorbent material extend in a longitudinal direction in a plane;

stretching the superabsorbent material transversely to the longitudinal direction of the slits, whereby the slits are widened to form openings having parts of superabsorbent material located on both sides of the openings twisted and rotated out of the plane to form edges projecting respectively upwardly and downwardly from said plane, whereby the superabsorbent material changes from a two-dimensional structure to a three-dimensional network structure; and bringing together the slits and stretched superabsorbent material with an absorbent body made from the group consisting of mat-formed cellulose, foamed material, and cellulose material from a pre-formed web.

* * * * *